(12) United States Patent
Rosenthal et al.

(10) Patent No.: US 6,174,701 B1
(45) Date of Patent: *Jan. 16, 2001

(54) NEURONAL FACTOR

(75) Inventors: Arnon Rosenthal, Pacifica; John W. Winslow, El Granada, both of CA (US)

(73) Assignee: Genentech, Inc., So. San Francisco, CA (US)

( * ) Notice: Under 35 U.S.C. 154(b), the term of this patent shall be extended for 0 days.

This patent is subject to a terminal disclaimer.

(21) Appl. No.: 08/455,741

(22) Filed: May 31, 1995

Related U.S. Application Data

(63) Continuation of application No. 08/381,030, filed on Jan. 31, 1995, which is a continuation of application No. 07/494,024, filed on Mar. 15, 1990, now abandoned, which is a continuation-in-part of application No. 07/449,811, filed on Dec. 12, 1989, now abandoned.

(51) Int. Cl.$^7$ .............................. C12N 15/00; C12N 5/02; C12P 21/06; C07H 21/04
(52) U.S. Cl. .................... 435/69.1; 536/23.5; 435/320.1; 435/325; 435/352; 435/354; 435/357; 435/358; 435/364; 435/366; 435/367; 435/252.3; 435/252.33; 435/69.7; 435/69.8

(58) Field of Search .............................. 435/6, 69.1, 69.8, 435/240.2, 252.3, 252.33, 320.1, 325, 352, 354, 357, 358, 364, 366, 367; 536/23.5, 24.3, 24.31, 24.33

(56) References Cited

U.S. PATENT DOCUMENTS 5,180,820 * 1/1993 Barde et al. ....................... 536/23.51
5,266,474 * 11/1993 Miller ................................... 435/226

* cited by examiner

*Primary Examiner*—Marianne P. Allen
(74) *Attorney, Agent, or Firm*—Knobbe, Martens, Olson & Bear LLP

(57) ABSTRACT

A novel polypeptide, designated neuronal factor (NF), has been identified by PCR amplification of human genomic DNA. Provided herein is nucleic acid encoding NF useful in diagnostics and in the recombinant preparation of NF. NF is used in the treatment of nerve cells and in diagnostic assays.

16 Claims, 4 Drawing Sheets

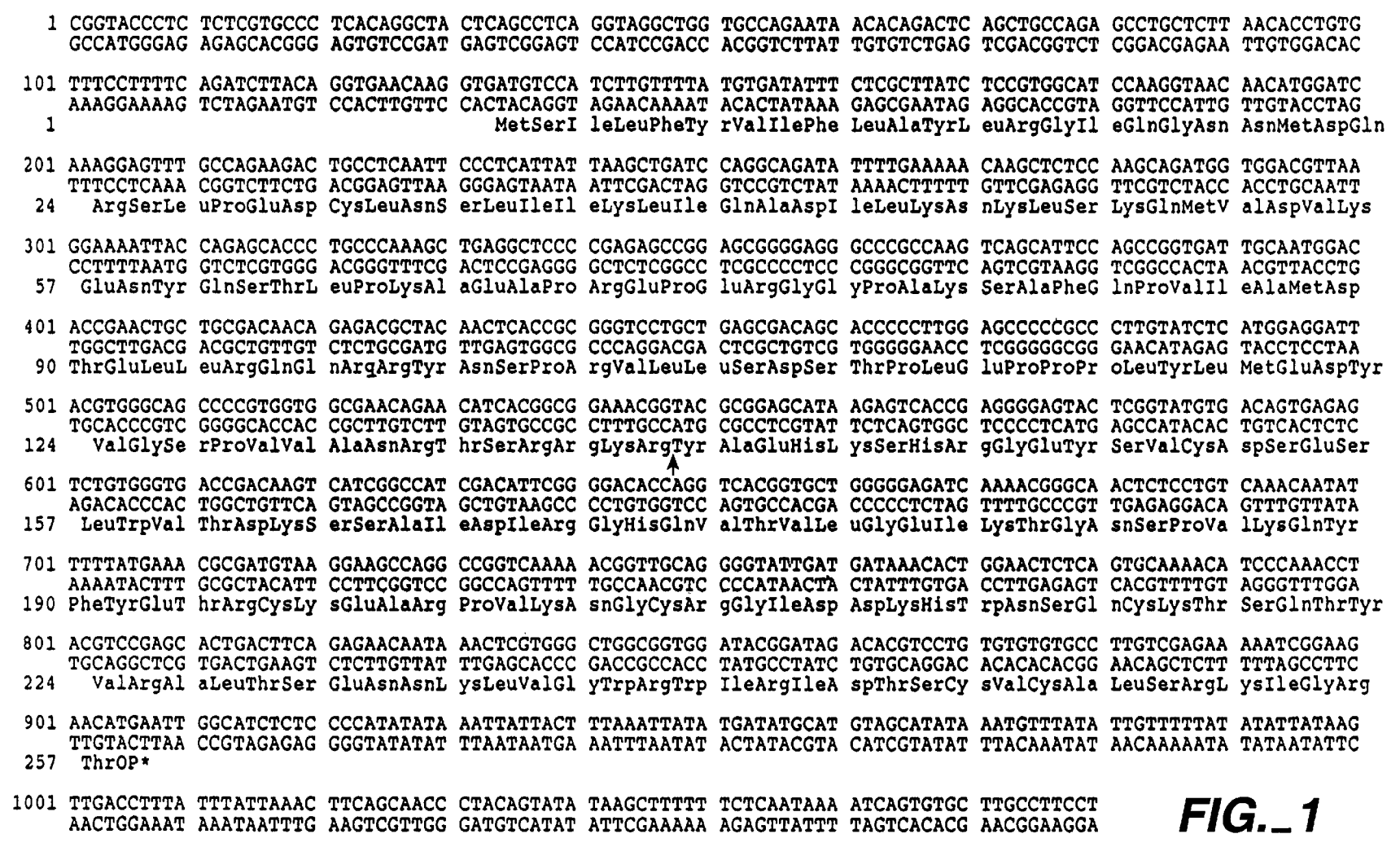

FIG._1

```
   1 GAATTCACTC GAGACGCGCC TTACTGGAAC TCCAGCACCG AATGGTGTGG ACACAGTTGA TTAGAGAGGT CGCAGGCTGG AATTGGAATC GAGATCTTAC
     CTTAAGTGAG CTCTGCGCGG AATGACCTTG AGGTCGTGGC TTACCACACC TGTGTCAACT AATCTCTCCA GCGTCCGACC TTAACCTTAG CTCTAGAATG

101 AGTGAACAA  GGTGATGTCC ATCTTGTTTT ATGTGATATT TCTTGCTTAT CTCCGTGGCA TCCAAGGCAA CAAACATGAT CAAAGGAGTT TGCCAGAAGA
     TCCACTTGTT CCACTACAGG TAGAACAAAA TACACTATAA AGAACGAATA GAGGCACCGT AGGTTCCGTT GTTGTACCTA GTTTCCTCAA ACGGTCTTCT
   1                                            MetSer      LeuArgLeu  eLeuAlaTyr leGlnGlyAs nAsnMetAsp GlnArgSerL euProGluAsp

201 CTCTCTAAT  TCCCTCATTA TCAAGTTGAT CCAGGCGGAT ATCTTGAAAA ACAAGCTCTC CAAGCAGATG GTAGATGTTA AGGAAAATTA CCAGAGCACC
     GAGAGAGTTA AGGGAGTAAT AGTTCAACTA GGTCCGCCTA TAGAACTTTT TGTTCGAGAG GTTCGTCTAC CATCTACAAT TCCTTTTAAT GGTCTCGTGG
  30 SerLeuAsn  SerLeuIleI  leLysLeuIl  eGlnAlaAsp  IleLeuLysA snLysLeuSe  rLysGlnMet  ValAspValL  ysGluAsnTy  rGlnSerThr

301 CTGCCCAAAG CAGAGAACCA CAGAGGGAG GTCGTCCGTG GTCTCCTCTC CAGGCCACGA GTCAGAATTC AGGCCACCAG TTGCAACAGA CACAGAACTA CTACGGCAAC
     GACGGGTTTC GTCTCTTGGT GTCTCCGTTG CAGCAGGACG GACCGGTGCT CAGTCTTAAG TCCGGTGGTC AACGTGTCT GTGTCTTGAT GATGCCGTTG
  63 LeuProLysA laGluAspPr oArgGluPro ArgValLeuL euSerAspSe rArgAlaGlu GlnProMetI leAlaThrAs pThrGluLeu GlnProMetI leAlaThrAs pThrGluLeu GlnArgGlnGln

401 AGAGACGCTA CAATTCACCC CGGTCCTGC TGAGTGACAG CACCCCTTTG GAGCCCCCTC AATGGAAGAT TATGTGCAA CCCCGGTGCT
     TCTCTGCGAT GTTAAGTGGG GCCCAGGACG ACTCACTGTC GTGGGGAAAC CTCGGGGGAG TTACCTTCTA ATACACCGTT GGGGCCACCA
  97 ArgArgTy   rAsnSerPro ArgValLeuL euSerAspSe rThrProLeu GluProProP roLeuTyrLe uMetGluAsp TyrValAlaT hrProValVal

501 AACCAATAGA ACATCACCAC GGAGGAAACG CATAAGAGTC ACCGAGGAGA GTACTCAGTG TGTGACCTGG AGAGCCTGTG GGTGACCGAC
     TTGGTTATCT TGTAGTGGTG CCTCCTTTGC GTATTCTCAG TGGCTCCTCT CATGAGTCAC ACACTGGACC TCTCGGACAC CCACTGGCTG
 130 ThrAsnArg  ThrSerProA  rgArgLysAr sHisLysSerH  isSerGlyVal TyrSerVal uTyrSerVal CysAspSerG luSerLeuTr pValThrAsp

601 AAGTCCTCAG CCATTGACAT TCGGGGACAC CAGGTTACAG TGTGGGAGA GATCAAAACC GGCAACTCTC CGGTTGAGAG CTGTGAAACA ATATTTTTAT GAAACGAGGT
     TTCAGGAGTC GGTAACTGTA AGCCCCTGTG GTCCAATGTC ACAACCCTCT CTAGTTTTGG CCGTTGAGAG GGAACCTCTC GACACTTTGT TATAAAAATA CTTTGCTCCA
 163 LysSerSerA laIleAspIl eArgGlyHis GlnValThrV alLeuGlyGl uIleLysThr GlyAsnSerP roValLysGl nTyrPheTyr GluThrArgCys

701 GTAAAGAAGC CAGGCCAGTC AAAAACGGTT TGATGACAAA GCAGGGGGAT CACTGGAACT CTCAGTGCAA AACGTCGCAA ACCTACGTCC GAGCACTGAC
     CATTTCTTCG GTCCGGTCAG TTTTTGCCAA ACTACTGTTT CGTCCCCCTA ACTACTGTTT GTGACCTTGA GAGTCACGTT TGGATGCAGG CTCGTGACTG
 197 LysGluAl   aArgProVal LysAsnGlyC ysArgGlyIl eAspAspLys HisTrpAsnS erGlnCysLy sThrSerGln ThrTyrValA rgAlaLeuThr

801 TTCAGAAAAC AACAAACTCG TAGGCTGGCG CTGGATACGA ATAGACACTT CCTGTGTGTG AGAAAATCG GAAGAACATG AATTGGCATC
     AAGTCTTTTG TTGTTTGAGC ATCCGACCGC GACCTATGCT TATCTGTGAA GGACACACAC TCTTTTAGC CTTCTTGTAC TTAACCGTAG
 230 SerGluAsn  AsnLysLeuV alGlyTrpAr gTrpIleArg IleAspThrS erCysValCy sAlaLeuSer ArgLysIleG lyArgThrOp *

901 TGTCCCACA  TATAAATTAT TACTTTAAAT GTATATGATAT GCATGTAGCA TATAAATGTT TTATATATTA TAAGTTGACC TTTATTTATT
     ACAGGGGTGT ATATTTAATA ATGAAATTTA CATATACTAT CGTACATCGT ATATTACAA AATATATAAT ATTCAACTGG AAATAATAA

1001 AAACTTCAGC AACCCTTACA GTATATAAGC AATAAAATTC GTGTGCTTGC CTTCGCTCAG CCCTCTCCA TTGTTTTGTG
     TTTGAAGTCG TTGGGAATGT CATATATTCG TTATTTTAAG CACACGAACG GAAGCGAGTC GGAGAGGGT AACAAAACAC

1101 ATTGGGTCT  TCTGTAAAAC CGGAACCCT TGTCAAGGCC CATTCAGTAT ATGACTCAGT TTTCAGTAAA CTTTCTAAA
     TAACCCAGA  AGACATTTG  GCCCTTGGGA GTAAGTCATA TACTGAGTCA AAAGTCATTT GAAAGATTT

1201 ATCGG
     TAGCC
```

FIG._2

```
hum NMF    1  MSILFYVIFLAYLRGIQGNNMDQRSLPEDSLNSLIIKLIQADILKNKLSK
hum BDNF   1  MTILFLTMVISYFGCMKAAPMKEANIRGQG--GLAYPGVRTHGTLESVNG
hum NGF    1  MSMLFYTLITAFLIGIQAEPHSESNVPAGH----TIPQHWTKLQHSLDT hum NMF   51  QMVDVKENYQSTLPKAEAPREPERGGPAKSAFQPVIAMDTELLRQQRRYN
hum BDNF  49  PKAGSRG-----LTSLADTFEHMIEELLDED-QKVRPNEEN--NKDADLY
hum NGF   47  ALRRAR-------SAPAAIAARVAGQTRN-----ITVDPRLFKK-RRLR
```

NMF
                                      NGF ←—↓—→ BDNF

```
hum NMF  101  SPRVLLSDSTPLEPPPLYMEDYVGSPVVANRTSRRKRYAEHKS-HRGEY
hum BDNF  91  TSRVMLSSQVPLEPPLLFLLEEYKNYLDAANMSMRVRRHSDPA--RRGEL
hum NGF   84  SPRVLFSTQPPREAADTQDLDFEVGGAAPFNRTHRSKRSSSHPIFHRGEF
```

├——B5-3——→

```
hum NMF  150  SVCDSESLWVT--DKSSAIDIRGHQVTVLGEIKTGNSPVKQYFYETRCKE
hum BDNF 139  SVCDSISEWVTAADKKTAVDMSGGTVTVLEKVPVSKGQLKQYFYETKCNP
hum NGF  134  SVCDSVSVWVG--DKTTATDIKGKEVMVLGEVNINNSVFKQYFFETKCRD
```

←——BA3——┤

```
hum NMF  198  ARPVKNGCRGIDDKHWNSQCKTSQTYVRALTSENNKLVGWRWIRIDTSCV
hum BDNF 189  MGYTKEGCRGIDKRHWNSQCRTTQSYVRALTMDSKKRIGWRFIRIDTSCV
hum NGF  182  PNPVDSGCRGIDSKHWNSYCTTTHTFVKALTMDG-KQAAWRFIRIDTACV
```

```
hum NMF  248  CALSRK-IGRT
hum BDNF 239  CTLTIK--RGR
hum NGF  231  CVLSRKAVRRA
```

*FIG._3*

NEURONAL FACTOR

This is a continuation of application(s) Ser. No. 08/831,030 filed on Jan. 31, 1995, which is a file wrapper continuation application of Ser. No. 07/494,024, filed Mar. 15, 1990, now abandoned, which was a continuation in part of application Ser. No. 07/449,811, filed Dec. 12, 1989, now abandoned, which applications are incorporated herein by reference and to which applicaitons(s) priority is claimed under 35 USC §120.

FIELD OF THE INVENTION

This application relates to proteins which are involved in the growth, regulation or maintenance of nervous tissue. In particular, it relates to nerve-derived factors having homology to NGF.

BACKGROUND OF THE INVENTION

Nerve growth factor (NGF) is a protein which has prominent effects on developing sensory and sympathetic neurons of the peripheral nervous systems. NGF acts via specific cells surface receptors on responsive neurons to support neuronal survival, promote neurite outgrowth, and enhance neurochemcial differentiation. NGF actions are accompanied by alterations in neuronal membranes (Connolly et al., J. Cell. Biol. 90:176–180 [1981]; Skaper and Varon, Brain Res. 197:379–389 [1980]), in the state of phosphorylation of neuronal proteins (Yu, et al., J. Biol. Chem. 255:10481–10492 [1980]; Haleqoua and Patrick, Cell 22:571–581 [1980]), and in the abundance of certain mRNAs and proteins likely to play a role in neuronal differentiation of function (see, for example, Tiercy and Shooter, J. Cell. Biol. 103:2367–2378 [1986]).

Forebrain cholinergic neurons also respond to NGF and may require NGF for trophic support. (Hefti, J. Neurosci., 6:2155 [1986]). Indeed, the distribution and ontogenesis of NGF and its receptor in the central nervous system (GNS) suggest that NGF acts as a target-derived neurotrophic factor for basal forebrain cholinergic neurons (Kosching, TINS, pp 570–573 (Nov/Dec [1986]).

While a number of animal homologues to NGF have become known, it was not until recently that an apparently distinct nerve growth factor was identified that nonetheless bears some homology to NGF (Leibrock et al., Nature 341:149 [1989]). This factor, called brain-derived neurotrophic factor (BDNF), was purified from pig brain, and a partial amino acid sequence determined both from the N-terminal end and from fragments purified after cleavages. The longest sequence, compiled from several overlapping fragments, was used to synthesize two sets of oligonucleotides that were used to prime the amplification of a pig genomic template using the polymerase chain reaction (PCR). The nucleotide sequence between the two primers was determined and used to synthesize specific primers for further PCRs on a complementary DNA template obtained by reverse transcription of total RNA isolated from the superior colliculus of the pig brain. The nucleotide sequence so obtained contained an open reading frame coding for a protein of 252 amino acids, starting with the first methionine codon found after four in-frame stop codons. Leibrock et al. speculate that there is no reason to think that BDNF and NGF should be the only members of a family of neurothrophic proteins having in common structural and functional characteristics, and the authors hope that these common structural features could be sued to aid the discovery of other members.

It is an object to identify other neurotrophic factors which bear homology to NGF and to obtain nucleic acid encoding such factors.

It is another object to synthesize such new factors in recombinant cell culture.

It is yet another object to provide derivatives and modified forms of such new factors.

It is an additional object to prepare immunogens for raising antibodies against such new factors, as well as to obtain antibodies capable of binding them.

Another object is to provide diagnostic and therapeutic compositions comprising such new factors or derivatives thereof and methods of therapeutic treatment.

SUMMARY OF THE INVENTION

These and other objects of the invention apparent to the ordinary artisan are accomplished by first providing a nucleic acid sequence comprising at least a portion of the coding sequence for a new nerve-derived factor related to NGF and BDNF, hereafter termed neuronal factor (NF). An alternative name for NF is neuronotrophin-3, or NT-3. The nucleic acid sequence is inserted into an expression vector and expressed in recombinant host cell culture in order to synthesize NF, or is used in hybridization assays for NF nucleic acid.

NF or fragments thereof (which also may by synthesized by in vitro methods) are fused (by recombinant expression or in vitro covalent methods) to an immunogenic polypeptide and this, in turn, is used to immunize an animal in order to raise antibodies against an NF epitope. Anti-NF is recovered from the serum of immunized animals. Alternatively, monoclonal antibodies are prepared from cells of the immunized animal in coventional fashion. Antibodies identified by routine screening will bind to NF but will not substantially cross-react with BDNF or NGF. Immobilized anti-NF antibodies are useful particularly in the diagnosis (in vitro or in vivo) or purification of NF.

Substitutional, delectional or insertional mutants of NF are prepared by in vitro or recombinant methods are screened for immuno-crossreactivity with NF and for NF antagonist or agonist activity.

NF also is derivatized in vitro in order to prepare immobilized NF and labelled NF particularly for purposes of diagnosis of NF or its antibodies, or for affinity purification of NF antibodies.

NF, tis derivatives or antibodies are formulated into physiologically acceptable vehicles, especially for therapeutic use. Such vehicles include sustained release formulations of NF.

In another aspect, the invention provides a method for producing NF, comprising culturing the transformed host cell and recovering NF from the culture.

NF has been found to be neurothrophic for primary sympathetic neurons, sensory neurons derived from nodose ganglion (placode), and subpopulations of spinal sensory neurons derived from dorsal root ganglion (neural crest). In addition, it has a broad tissue distribution and is structurally related to both NGF and BDNF. NF has a unique range of trophic activities that complement those of NGF and BDNF, and is a differentiation-inducing factor for the phaeochromacytoma cell line, PC-12. Thus, it is likely to play a wide role in defining the fate and function of nerve cells during development. In addition, its presence in the CNS indicates that it can be useful as a therapeutic agent for neurodegenerative diseases and damaged nerves, e.g., nerves damaged as a result of trauma.

BRIEF DESCRIPTION OF THE DRAWINGS

FIG. 1 depicts the complete nucleotide sequence for the human NF gene and the deduced amino acid sequence. The arrow indicates where the mature sequence begins.

FIG. 2 depicts the complete nucleotide sequence for the rat NF gene and the deduced amino acid sequence. The arrow indicates where the mature sequence begins.

FIG. 3 aligns the homologous amino acid sequences among human NF, NGF, and BDNF. The locations of the sense (B5-3) and antisense (BA3) primer sites on the sequence are marked with vertical solid arrows, and a hypothetical upstream processing site in NF is marked with open arrows.

DETAILED DESCRIPTION OF THE PREFERRED EMBODIMENTS

Figure 4A:
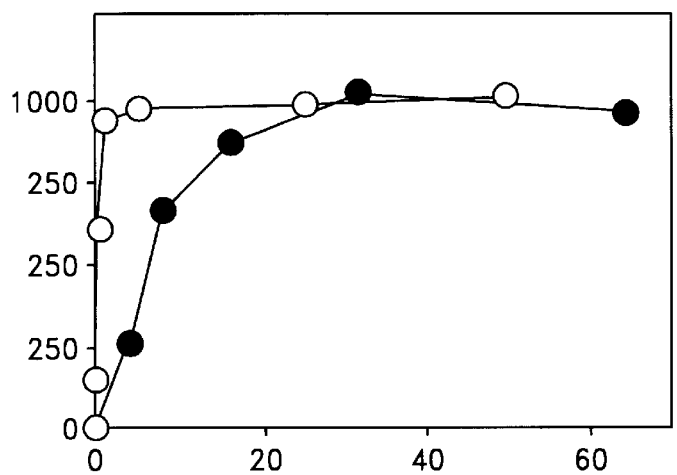
FIG. 4 shows graphs of NGF-dependent (open circles) or NF-dependent (solid circles) neurite outgrowth from chick embryonic day-10 (A) sympathetic neurons, (B) nodose ganglia neurons, and (C) dorsal root ganglia neurons.

NF is defined to be a polypeptide encoded by the mature human NF nucleotide sequence set forth in FIG. 1, fragments thereof having greater than about 5 residues comprising an immune epitope of NF, amino acid sequence variants of said FIG. 1 sequence wherein an amino acid residue has been inserted N- or C-terminal to, or within, said FIG. 1 sequence or its fragment as defined above, and/or amino acid sequence variants of said FIG. 1 sequence or its fragment as defined above wherein an amino acid residue of said FIG. 1 sequence or fragment thereof has been substituted by another residue, including other animal species of NF such as rat preproNF, and derivatives of NF or its fragments as defined above wherein the NF or its fragments have been covalently modified by substitution with a moiety other than a naturally occurring amino acid; provided, however, that such fragment or variant is novel and unobvious over the prior art, and is not NGF or BDNF of any animal species or any known fragment of such NGF or BDNF. Mature NF amino acid sequence variants generally will be about 75% (and usually >85%) homologous on an identical residue basis after aligning (introducing any necessary spaces) to provide maximum homology.

NF nucleic acid is defined as RNA or DNA which encodes a NF polypeptide or which hybridizes to such DNA and remains stably bound to it under stringent conditions and is greater than about 10 bases in length, provided, however, that such hybridizing nuclic acid is novel and unobvious over any prior art nucleic acid including that which encodes or is complementary to nucleic acid encoding BDNF or NGF. Stringent conditions are those which (1) employ low ionic strength and high temperature for washing, for example, 0.15 M Nacl/0.015 M sodium citrate/0.1% NaDodSO$_4$ at 50° C., or (2) use during washing a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM Nacl, 75 mM sodium citrate at 42° C.

DNA encoding NF is obtained from brain tissue cDNA libraries, or genomic DNA, or by in vitro synthesis. Hybridizing nucleic acid generally is obtained by invitro synthesis. Identification of NF DNA most conveniently is accomplished by probing human cDNA or genomic libraries by labelled oligonucleotide sequences selected from the FIG. 1 sequence in accord with known criteria, among which is that the sequence should be of sufficient length and sufficiently unambiguous that false positives are minimized. Typically, a $^{32}$P labelled oligonucleotide having about 30 to 50 bases is sufficient, particularly if the oligonucleotide contains one or more codons for methionine or typtophan. Isolated nucleic acid will be DNA that is identified and separated from contaminant nucleic acid encoding other polypeptides from the source of nucleic acid. The nucleic acid may be labelled for diagnostic purposes.

Amino acid sequence variants of NF are prepared by introducing appropriate nucleotide changes into the NF DNA, or by in vitro synthesis of the desired NF. Such variants include, for example, deletions from, or insertions or substitutions of, residues within the amino acid sequence shown for mature, human NF in FIG. 1. Any combination of delection, insertion, and substitution is made to arrive at the final construct, provided that the final construct possesses the desired characteristics. The amino acid changes also may result in further modifications of NF upon expression in recombinant hosts, e.g. introducing or moving sites of glycosylation, or introducing membrane anchor sequences (in accordance with U.S. Ser. No. 07/083,757, filed Aug. 6, 1987, which is equivalent to PCT WO 89/01041 published Feb. 9, 1989).

There are two principal variables in the construction of amino acid sequence variants: the location of the mutation site and the nature of the mutation. These are variants from the FIG. 1 sequence, and may represent naturally occurring alleles (which will not require manipulation of the NF DNA) or predetermined mutant forms which are made by mutating the DNA, either to arrive at an allele or a variant that is not found in nature. In general, the location and nature of the mutation chosen will depend upon the NF characteristic to be modified. For example, candidate NF antagonists or supper agonists will be initially selected by locating sites that are identical or highly conserved among NGF, BDNF and NF. These sites then will be modified in series, e.g., by (1) substituting first with conservative choices and then with more radical selections depending upon the results achieved, (2) deleting the target residue, or (3) inserting residues of the same or different class adjacent to the located site, or combinations of options 1–3. One helpful technique is called "ala scanning". Here, a residue or group of target residues are identified and substituted by alanine or polyalanine. Those domains demonstrating functional sensitivity to the alanine substitutions then are refined by introducing further or other variants at or for the sites of alanine substitution. Obviously, such variations which, for example, convert NF into NGF or BDNF are not included within the scope of this invention, nor are any other NF variants or polypeptide sequences that are not novel and unobvious over the prior art. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed NF variants are screened for the optimal combination of desired activity.

Amino acid sequence deletions generally range from about 1 to 30 residues, more preferably about 1 to 10 residues, and typically are contiguous. Deletions may be introduced into regions of low homology among BDNF, NGF and NF in order to modify the activity of NF. Deletions from NF in areas of substantial homology with BDNF and NGF will be more likely to more significantly modify the biological activity of NF.

Amino acid sequence insertions include amino- and/or carboxyl-terminal fusions ranging in length from one residue to polypeptides containing a thousand or more residues, as well as intrasequence insertions of single or multiple amino acid residues. Intrasequence insertions (i.e., insertions within the mature NF sequence) may range generally from about 1 to 10 residues, more preferably 1 to 5, most preferably 1 to 3. An example of a terminal insertion includes fusion of a heterologous N-terminal signal sequence to the N-terminus of the NF molecule to facilitate the secretion of mature NF from recombinant hosts. Such signals generally will be homologus to the intended host cell and include STII or 1 pp for *E. coli,* alpha factor for yeast and viral signals such as herpes gD for mammalian cells. Other insertions include the fusion of an immunogenic polypeptide such as a bacterial or yeast protein to the N- or C-termini of NF.

The third group of variants are those in which at least one amino acid residue in the NF molecule, and preferably only one, has been removed and a different residue inserted in its place. An example is the replacement of arginine and lysine by other amino acids to render the NF resistant to proteolysis by serine porteases, thereby crating a more stable NF analogue. The sites of greatest interest for substitutional mutagenesis include sites where the maino acids found in BDNF, NGF and NF are substantially different in terms of side chain bulk, charge or hydrophobicity, but where there also is a high degree of homology at the selected site within various animal analogues of NGF and BDNF (e.g., among all the animal NGFs on the one hand and all the BDNFs on the other). This analysis will highlight residues that may be involved in the differentiation of activity of the trophic factors, and therefore, variants at these sites may affect such activities. Examples of such NF sites, numbered from the mature N-terminal end, and exemplary substitutions include NF ($N_{85} \rightarrow$ K, H, Q or R) and NF ($D_{72} \rightarrow$ E, F, P, Y or W). Other sites of interest are those in which the residues are identical among all animal species' BDNF, NGF and NF, this degree of conformation suggesting importance in achieving biological activity common to all three factors. These sites, especially those falling within a sequence of at least 3 other identically converved sites, are substituted in a relatively conservative manner. Such conservative substitutions are shown in Table 1 under the heading of preferred substitutions. If such substitutions result in a change in biological acitivyt, then more substantial changes, denominated exemplary substitutions in Table 1, or as further described below in reference to amino acid classes, are introduced and the products screened.

TABLE 1

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg; | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |

TABLE 1-continued

| Original Residue | Exemplary Substitutions | Preferred Substitutions |
|---|---|---|
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Sites particularly suited for conservative substitutions include, numbered from the N-terminus of the mature NF, $R_8$, $G_9$, $E_{10}$, $S_{12}$, $V_{13}$, $D_{15}$, $S_{16}$, $W_{20}$, $V_{21}$, $D_{23}$, $K_{24}$, $V_{37}$, $L_{38}$, $K_{49}$, $Q_{50}$, $Y_{51}$, $F_{52}$, $Y_{53}$, $E_{54}$, $T_{55}$, $G_{66}$, $R_{68}$, $G_{69}$, $I_{70}$, $D_{71}$, $H_{74}$, $W_{75}$, $N_{76}$, $S_{77}$, $A_{88}$, $L_{89}$, $T_{90}$, $W_{99}$, $R_{100}$, $I_{102}$, $R_{103}$, $I_{104}$, $D_{105}$, and $T_{106}$. Cysteine residues not involved in maintaining the proper conformation of NF also may be substituted, generally with serine, in order to improve the oxidative stability of the molecule and prevent aberrant crosslinking. Sites other than those set of in this paragraph are suitable for deletional or insertional studies generally described above.

Substantial modifications in function or immunological identity are accomplished by selecting substitutions that differ significantly in their effect on maintaining (a) the structure of the polypeptide backbone in the area of the substitution, for example, as a sheet or helical conformation, (b) the charge of hydrophobicity of the molecule at the target site, or (c) the bulk of the side chain. Naturally occurring residues are divided into groups based on common side chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro;
(6) aromatic: trp, tyr, phe.

Non-conservative substitutions will entail exchanging a member of one of these classes for another. Such substituted residues also may be introduced into the conservative substitution sites set forth above or, more preferably, into the remaining (non-conserved) sites.

Examples of NF variants include NF ($E_{59}A_{60}R_{61} \rightarrow$ NAS or NAT) (this adds an N-linked glycosylation site); NF($D_{72}$—$Q_{83}$); NF($Y_1$—$C_{57}$) (variants so depicted are fragments containing the residues indicated); NF($Y_1$—$C_{14}$); NF($C_{14}$—$C_{57}$); NF($C_{14}$—$C_{57}$); NF($C_{14}$—$C_{79}$); NF($C_{14}$—$C_{108}$); NF($C_{14}$—$C_{100}$); NF($R_8$—$K_{24}$); NF($R_8$—$R_{31}$); NF($R_{31}$—$R_{56}$); NF($C_{57}$—$C_{67}$); NF($K_{58}$—$C_{57}$); NF($C_{67}$—$C_{108}$); NF($C_{67}$—$C_{79}$); NF($C_{79}$—$C_{108}$); NF($C_{57}$—$G_{66}$); NF($R_{68}$—$C_{79}$); NF($K_{80}$—$C_{108}$); NF($K_{80}$—$K_{95}$); NF($R_{87}$—$R_{100}$); NF($R_{87}$—$K_{95}$); NF($T_{90}$—$R_{100}$); NF($Y_1$—$C_{110}$) V L T V K R V R R; NF($V_{48}$—$C_{110}$) V L T V K R V R R; NF($V_{48}$—$C_{110}$) S L T I K R I R A; NF($V_{48}$—$C_{110}$) T L S R K A G R R A; D D D D S P I A R R G E I S V C D S V S D W V S A P D K D T A V D I K G D D V M V L K K V G I N H S V [NF($V_{48}$—$C_{110}$)]; hNGF($S_1$—$V_{48}$) NF($V_{48}$—$C_{110}$) hNGF($V_{109}$—$A_{120}$); BDNF($R_7$—$Q_{48}$) NF(V48—$C_{110}$) BDNF($V_{110}$—$R_{119}$); NF($\Delta C_{57}$); NF($\Delta C_{67}$); NF($\Delta Q_{50}$—$\Delta T_{55}$) (variants depicted in this fashion comprise deletions of the indicated span of residues, inclusive); NF($\Delta R_{68}$—$\Delta D_{71}$); NF($\Delta H_{74}$—$\Delta S_{77}$); NF($\Delta W_{99}$—$\Delta T_{106}$); NF($_{58}$→H); NF($E_{58}$→G); NF($A_{60}$→I); NF($R_{61}$→D); NF($N_{65}$→T); NF($D_{72}$→N); NF($K_{80}$→H); NF($N_{93}$→D); NF($L_{96}$→F, Y, I or V); NF($V_{97}$→F); NF($\Delta N_{94}$); NF($G_{55}GC_{67}$); NF($K_{73}$→Q, H, N, T, Y or W); and NF($D_{105}$→E, N, Q, Y, S or T).

Also included is NF wherein position 59 is substituted with an amino acid residue other than E, D or P; position 60 with other than A, P or M; position 72 with other than D, S or K; and/or position 93 with other than N, G or S; as well as cyclized NF fragments, including cyclic polypeptides comprising the sequences IKTG, EIKTG, EIKTGN, SPV, SPVK, HQV, KSS, KSSA, YAEHKS, RYAEHKS, RYAEHKSH, YAEHKSH, ANRTS, NRT, ANRT, NRTS, KEA, KEAR, KEARP, IDDK, SENN, TSENN, TSENNK or KLVG.

Also within the scope hereof are BDNF and NGF amino acid variants have analogous structures to the NF variants set forth herein. For example, the analogous positions of NGF and BDNF are substituted with a residue other than D or P, respectively, in analogy to the same mutation at position 59 of NF.

DNA encoding NF variants preferably is prepared by site-specific mutagenesis of DNA that encodes an earlier prepared variant or a nonvariant version of NF. Site-specific mutagenesis allows the production of NF variants through the use of specific ologonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA,* 2:183 (1983).

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA,* Editor A. Walton, Elsevier, Amsterdam (1981), the disclosure of which is incorporated herein by reference. These phage are readily commercially available and their use is generally well known to those skilled in the art. Also, plasmid vectors that contain a single-stranded phage origin of replication (Veira et al., *Meth. Enzymol.* 153:3 [1987]) may be employed to obtain single-stranded DNA. Alternatively, nucleotide substitutions are introduced by synthesizing the appropriate DNA fragment in vitro and amplifying it by polymerase chain reaction (PCR) procedures known per se in the art.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (USA), 75:5765 (1978). The primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated region may be removed and placed in an appropriate vector for protein production, generally an expression vector of the type that is typically employed for transformation of an appropriate host.

Most deletions and insertions, and substitutions in particular, are not expected to produce radical changes in the characteristics of the NF molecule, and single substitutions will preserve at least one immune epitope in the NF polypeptide.

Since it is often difficult to predict in advance the characteristics of a variant NF, it will be appreciated that some screening will be needed to select the optimal variant. One can screen for enhanced trophic activity, differential neuron cell type specificity, stability in recombinant cell culture or in plasma (e.g. against proteolytic cleavage), possession of antagonist activity, oxidative stability, ability to be secreted in elevated yields, and the like. For example, a change in the immunological character of the NF molecule, such as affinity for a given antibody, is measured by a competitive-type immunoassay. Changes in the enhancement or suppression of neurotrophic activities by the candidate mutants are measured by dendrite outgrowth or explant cell survival assays. Modifications of such protein properties as redox or thermal stability, hydrophobicity, susceptibility to proteolytic degradation, or the tendency to aggregate with carriers or into multimers are assayed by methods well known in the art.

Trypsin or other protease cleavage sites are identified by inspection of the encoded amino acid sequence for paired basic residues, e.g. combinations of adjacent arginyl and lysinyl residues. These are rendered inactive to protease by substituting one of the residues with another residue, preferably a basic residue such as glutamine or a hydrophobic residue such as serine; by deleting one or both of the basic residues; by inserting a prolyl residue immediately after the last basic residue; or by inserting another residue between the two basic residues.

A variant NF typically is made by site-specific mutagenesis of the native NF-encoding nucleic acid, expression of the variant nucleic acid in recombinant cell culture, and, optionally, purification from the cell culture, for example, by bioassay of the variant's acitivty or by immunaffinity adsorption on a rabbit polyclonal anti-NF column (to absorb the variant by binding it to at least one remaining immune epitope). Small fragments, on the order of 40 residues or less, are conveniently made by in vitro methods.

The NF-encoding nucleic acid, whether variant or cDNA, then is ligated into a replicable vector for further cloning or for expression. Vectors are useful for performing two functions in collaboration with compatible host cells (a host-vector system). One function is to facilitate the cloning of the nucleic acid that encodes the NF, i.e., to produce usable quantities of the nuclic acid. The other function is to direct the expression of NF. One or both of these functions are performed by the vector-host system. The vectors will contain different components depending upon the function they are to perform as well as the host cell that is selected for cloning or expression.

Each vector will contain nucleic acid that encodes NF as described above. Typically, this will be DNA that encodes the NF in its mature form lined at its amino terminus to a secretion signal. This secreting signal preferably is the NF presequence that normally directs the secretion of NF from human cells in vivo. However, suitable secretion signals also include signals from other animal NF, viral signals or signals from secreted polypeptides of the same or related species.

Expression and cloning vectors contain a nucleic acid sequence that enables the vector to replicate in one or more selected host cells. Generally, in cloning vectors this sequence is none that enables the vector to replicate independently of the host chromosomes, and includes origins of replication or autonomously replicating sequences. Such sequences are well-known for a variety of bacteria, yeast and viruses. The origin of replication from the well-known plasmid pBR322 is suitable for most gram negative bacteria, the $2\mu$ plasmid origin for yeast and various viral origins (SV40, polyoma, adenovirus, VSV or BPV) are useful for cloning vectors in mammalian cells. Origins are not needed for mammalian expression vectors (the SV40 origin is used in the Examples only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even through it is not capable of replicating independently of the host cell chromosome.

DNA also is cloned by inserting into the host genome. This is readily accomplished with bacillus species, for example, by including in the vector a DNA sequence that is complementary to a sequence found in bacillus genomic DNA. Transaction of bacillus with this vector results in homologous recombination with the genome and inserting of NF DNA. However, the recovery of genomic DNA encoding NF is more complex than that of an exogenously replicated vector because restriction enzyme digestion is required to excise the NF DNA.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

A suitable selection gene for use in yeast is the trp1 gene present in the yeast plasmid YRp7 (Stinchcomb et al., 1979, "Nature" 282:39; Kingsman et al., 1979, "Gene" 7:141; or Tschemper et al., 1980, "Gene" 10:157). The trp1 gene provides a selection marker for a mutant strain of yeast lacking the ability to grow in tryptophan, for example, ATCC No. 44076 or PEP4-1 (Jones, 1977, "Genetics" 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

Examples of suitable selectable markers for mammalian cells are dihydrofolate reductase (DHFR) or thymidine kinase. Such markers enable the identification of cells which were competent to take up the NF nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes NF. Amplification is the process by which genes in greater demand for the production of a protein critical for growth are reiterated in tandem within the chromosomes of successive generations of recombinant cells. Increased quantities of NF are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, 1980, "Proc. Nat'l. Acad. Sci. USA" 77:4216. A particularly useful DHFR is a mutant DHFR that is highly resistant to MTX (EP 117,060A). This selection agent can be used with any otherwise suitable host, e.g. ATCC No. CCL61 CHO-K1, notwithstanding the presence of endogenous DHFR. The DHFR and NF-encoding DNA then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding NF, wild-type DHFR, and another selectable marker such as the neo gene can be identified using a selection agent for the selectable marker such as G418 and then selected and amplified using methotrexate in a wild-type host that contains endogenous DHFR.

Other methods, vectors and host cells suitable for adaptation to the synthesis of the hybrid receptor in recombinant vertebrate cell culture are described in M. J. Gething et al., "Nature" 293:620–625 (1981); N. Mantei et al., "Nature" 281:40–46 (1979); and A. Levinson et al., EP 117,060A and 117,058A. A particularly useful plasmid for mammalian cell culture expression of NF is pRK5 (EP publication no. 307,247).

Expression vectors, unlike cloning vectors, should contain a promoter which is recognized by the host organism and is operably linked to the NF nucleic acid. Promoters are untranslated sequences located upstream from the start codon of a structural gene (generally within about 100 to 1000 bp) that control the trasncription and translation of nucleic acid under their control. They typically fall into two classes, inducible and constitutive. Inducible pormoters are promoters that initiate increased levels of trasncription from DNA under their control in response to some change in culture conditions, e.g. the presence or absence of a nutrient or a change in temperature. At this time a large number of promoters recognized by a variety of potential host cells are well known. These pormoters are operably linked to NF-encoding DNA by removing them from their gene of origin by restriction enzyme digestion, followed by insertion 5' to the start codon for NF. This is not to say that the genomic NF promoter is not usable. However, heterologous promoters generally will result in greater transcription and higher yields of expressed NF.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the trasncription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exist then synthetic oligonucleotide adaptors or linkers are used in accord with conventional practice.

Promoters suitable for use with prokaryotic hosts include the β-lactamase and lactose promoter systems (Chan et al., 1978, "Nature" 275:615; and Goeddel et al., 1979, "nature" 281:544), alkaline phosphatase, a tryptophan (trp) promoter system (Goeddel, 1980, "Nucleic Acids Res." 8:4057 and EPO Appln. Publ. No. 36,776) and hybrid promoters such as the tac promoter (H. de Boer et al., 1983, "Proc. nat'l. Acad. Sci. USA" 80:21–25). However, other known bacterial promoters are suitable. Their nucleotide sequences have been published, thereby enabling a skilled worker operably to ligate them to DNA encoding NF (Siebenlist et al., 1980, "Cell" 20:269) using linkers or adaptors to supply any required restriction sites. Promoters for use in bacterial systems also will contain a Shine-Dalgarno (S. D.) sequence operably linked to the DNA encoding NF.

Suitable promoting sequences for use with yeast hosts include the promoters for 3-phosphoglycerate kinase (Hitzeman et al., 1980, "J. Biol. Chem." 255:2073) or other glycolytic enzymes (Hess et al., 1968, "J. Adv. Enzyme Reg." 7:149; and Holland, 1978, "Biochemistry" 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible pormoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

NF transcription from vectors in mammalian host cells is controlled by promoters obtained from the genomes of viruses such as polyma, cytomegalovirus, adenovirus, retroviruses, hepatitis-B virus and most preferably Simian Virus 40 (SV40), or from heterologous mammalian promoters, e.g. the action promoter. The early and late promoters of the SV40 virus are conveniently obtained as an SV40 restriction fragment which also contains the SV40 viral origin of replication (Fiers et al., 1978, "Nature" 273:113). Of course, promoters from the host cell or related species also are useful herein.

Transcription of NF-encoding DNA by higher eukaryotes is increased by inserting an enhancer sequence into the vector. An enhancer is a nucleotide sequence, usually about from 10–300 bp, that acts on a promoter to increase its trasncription and does so in a manner that is relatively orientation and position independent. Many enhancer sequences are no known from mammalian genes (globin, elastase, albumin, α-fetoproein and insulin). Typically, however, one will use an enhancer from a eukaryotic cell virus. Examples include the SV40 enhancer on the later side of the replication origin (bp 100–270), the cytomegalovirus early promoter enhancer, the polyoma enhancer on the later side of the replication origin, and adenoviral enhancers. The enhancer may be spliced into the vector at a position 5' or 3' to the NF-encoding sequence, but is preferably located at a site 5' from the promoter.

Expression vectors used in eukaryotic host cells (yeast, fungi, insect, plant, animal, human or nucleated cells from other multicellular organisms) will also contain sequences necessary for the termination of transcription and for stabilizing eh mRNA. Such sequences are commonly available from the 5' and, occasionally 3' untranslated regions of eukaryotic or viral DNAs or cDNAs. These regions contain regions that are transcribed as polyadenylated segments in the untranslated portion of the mRNA encoding NF. The 3' untranslated regions also include transcription termination sites.

Suitable host cells for cloning or expressing the vectors herein are the prokaryote, yeast or higher eukaryote cells described above. Suitable prokaryotes include gramnegative or gram positive organisms, for example E. coli or bacilli. A preferred cloning host is E. coli 294 (ATCC 31,446) although other gram negative or gram positive prokaryotes such as E. coli B, E. coli X1776 (ATCC 31,537), E. coli W3110 (ATCC 27,325), pseudomonas species, or Serratia Marcesans are suitable.

In addition to prokaryotes, eukaryotic microbes such as filamentous fungi or yeast or suitable hosts for NF-encoding vectors. Saccharomyces cerevisiae, or common baker's yeast, is the most commonly used among lower eukaryotic host microorganisms. However, a number of other genera, species and strains are commonly available and useful herein.

Suitable host cells for the expression of NF are derived from multicellular organisms. Such host cells are capable of complex processing and glycosylation activities. In principle, any higher eukaryotic cell culture is workable, whether from vertebrate or invertebrate culture, although cells from mammals such as humans are preferred. Propagation of such cells in culture is per se well known. See Tissue Culture, Academic Press, Kruse and Patterson, editors (1973). Examples of useful mammalian host cell lines are VERO and HeLa cells, Chinese hamster ovary cell lines, the WI38, BHK, COS-7, MDCK cell lines and human embryonic kidney cell line 293.

Host cells are transformed with the above-described expression or cloning vectors and cultured in conventional nutrient media modified as is appropriate for inducing promoters or selecting transformants containing amplified genes. The culture conditions, such as temperature, pH and the like, suitably are those previously used with the host cell selected for cloning or expression, as the case may be, and will be apparent to the ordinary artisan.

Covalent modifications of NF molecules are included within the scope of the invention. Variant NF fragments having up to about 40 residues may be conveniently prepared by in vitro synthesis. In addition, covalent modifications are introduced into the molecule by reacting targeted amino acid residues of the NF polypeptide with an organic derivatizing agent that is capable of reacting with selected side chains or the N- or C-terminal residues.

Cysteinyl residues most commonly are reacted with α-haloacetates (and corresponding amines), such as chloracetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfinde, methyl 2-pyridyl disulfide, p-chloromercuribenzoate, 2-chloromercuri-4-nitropenol, or chloro-7-nitrobenzo-2-oxa-1,3-diazole.

Histidyl residues are derivatized by reaction with diethylpro-carbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues including imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepared labeled proteins for use in radioimmunoassay, the chloramine T method described above being suitable.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking NF to a water-insoluble support matrix or surface for use in the method for purifying anti-NF antibodies, and vice versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl) dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group. NF also is covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

NF preferably is recovered from the culture medium as a secreted protein, although it also may be recovered from host cell lysates when directly expressed without a secretory signal. When NF is expressed in a recombinant cell other than one of human origin, the NF is thus completely free of proteins of human origin. However, it is necessary to purify NF from recombinant cell proteins in order to obtain preparations that are substantially homogeneous as to protein. As a first step, the culture medium or lysate is centrifuged to remove particulate cell debris. NF thereafter is purified from contaminant soluble proteins, for example, by fractionation on immunoaffinity or ion exchange columns; ethanol precipitation; reverse phase HPLC; chromatography on silica or on a cation exchange resin such as DEAE; chromatofocusing; SDS-PAGE; ammonium sulfate precipitation; or gel electrophoresis using, for example, Sephadex G-75. NF variants in which residues have been deleted, inserted or substituted are recovered in the same fashion as native NF, taking account of any substantial changes in properties occasioned by the variation. For example, preparation of an NF fusion with another protein, e.g. a bacterial or viral antigen, facilitates purification because an immunoaffinity column containing antibody to the antigen can be used to adsorb the fusion. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native NF may require modification to account for changes in the character of NF or its variants upon expression in recombinant cell culture.

NF also may be entrapped in microcapsules prepared, for example, by coacervation techniques or by interfacial polymerization, for example, hydroxymethylcellulose or gelatin-microcapsules and poly (methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, Osol, A., Ed., (1980).

NF is believed to find use as an agent for enhancing the survival of nerve cells. It, therefore, is useful in the therapy of degenerative disorders of the nervous system ("neurodegenerative diseases"), including such diseases as Alzheimer's disease, Parkinson's disease, Huntington's chorea, ALS, and other conditions characterized by necrosis or loss of neurons. In addition, it may be useful for treating damaged nerves, e.g., nerves damaged by traumatic conditions such as burns and wounds. It also is useful as a component of culture media for use in culturing nerve cells in vitro. Finally, NF preparations are useful as standards in assays for NF and in competitive-type receptor binding assays when labelled with radioiodine, enzymes, fluorophores, spin labels, and the like.

Therapeutic formulations of NF are prepared for storage by mixing NF having the desired degree of purity with optional physiologically acceptable carriers, excipients or stabilizers (*Remington's Pharmaceutical Sciences,* supra, in the form of lyophilized cake or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

NF to be used for in vivo administration must be sterile. This is readily accomplished by filtration through sterile filtration membranes, prior to or following lyophilization and reconstitution. NF ordinarily will be stored in lyophilized form.

Therapeutic NF compositions generally are placed into a container having a sterile access port, for example, an intravenous solution bag or vial having a stopper pierceable by a hypodermic injection needle.

NF optionally is combined with or administered in concert with other neurotrophic factors including NGF and/or BDNF and is used with other conventional therapies for degenerative nervous disorders.

The route of NF or NF antibody administration is in accord with known methods, e.g. injection or infusion by intravenous, intraperitoneal, intracerebral, intramuscular, intraocular, intraarterial or intralesional routes, topical administration, or by sustained release systems as noted below. NF is administered continuously by infusion into the fluid reservoirs of the CNS, although bolus injection is acceptable. NF preferably is administered into the ventricles of the brain or otherwise introduced into the CNS or spinal fluid. It should be administered by an indwelling catheter using a continuous administration means such as a pump, or it can be administered by implantation, e.g., intracerebral implantation, of a sustained release vehicle.

More specifically, NF can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer patients and animal models for Parkinson's disease described by Harbaugh, *J. Neural Transm. Suppl.*, 24: 271–277 (1987) and DeYebenes et al., *Mov. Disord.*, 2: 143–158 (1987), the disclosures of which are incorporated herein by reference. NF antibody is administered in the same fashion, or by administration into the blood stream or lymph.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et al., 1983, "Biopolymers" 22 (1): 547–556), poly (2-hydroxyethyl-methacrylate) (R. Langer, et al., 1981, "J. Biomed. Mater. Res." 15: 167–277 and R. Langer, 1982, "Chem. Tech." 12: 98–105), ethylene vinyl acetate (R. Langer et al., Id.) or poly-D-(-)-3-hydroxybutyric acid (EP 133,988A). Sustained release NF compositions also include liposomally entrapped NF. Liposomes containing NF are prepared by methods known per se: DE 3,218,121A; Epstein et al., 1985, "Proc. Natl. Acad. Sci. USA" 82: 3688–3692; Hwang et al., 1980, "Proc. Natl. Acad. Sci. USA" 77: 4030–4034; EP 52322A; EP 36676A; EP 88046A; EP 143949A; EP 142641A; Japanese patent application 83-118008; U.S. Pat. Nos. 4,485,045 and 4,544,545; and EP 102,324A. Ordinarily the liposomes are of the small (about 200–800 Angstroms) unilamelar type in which the lipid content is greater than about 30 mol. % cholesterol, the selected proportion being adjusted for the optimal NF therapy.

An effective amount of NF to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Typically, the clinician will administer NF until a dosage is reached that repairs, maintains, and, optimally, reestablishes neuron function. The progress of this therapy is easily monitored by conventional assays.

Polyclonal antibodies to NF generally are raised in animals by multiple subcutaneous (sc) or intraperitoneal (ip) injections of NF and an adjuvant. It may be useful to conjugate NF or a fragment containing the target amino acid sequence to a protein which is immunogenic in the species to be immunized, e.g., keyhole limpet hemocyanin, serum albumin, bovine thyroglubulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N\!=\!C\!=\!NR$.

Animals are immunized against the immunogenic conjugates or derivatives by combining 1 mg or 1 $\mu$g of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's complete adjuvant by subcutaneous injection at multiple sites. 7 to 14 days later animals are bled and the serum is assayed for anti-NF titer. Animals are boosted until the titer plateaus. Preferably, the animal is boosted with the conjugate of the same NF polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by EB virus transformation and screening for clones expressing the desired antibody.

NF antibodies are useful in diagnostic assays for NF or its antibodies. The antibodies are labelled in the same fashion as NF described above and/or are immobolized on an insoluble matrix. In one embodiment of a receptor binding assay, an antibody composition which binds to all or a selected plurality of members of the NF family is immobilized on an insoluble matrix, the test sample is contacted with the immobilized antibody composition in order to adsorb all NF family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

NF antibodies also are useful for the affinity purification of NF from recombinant cell culture or natural sources. NF antibodies that do not detectably cross-react with NGF or BDNF can be used to purify NF free from these other family members.

Suitable diagnostic assays for NF and its antibodies are well known per se. In addition to the bioassay described above, competitive, sandwich and steric inhibition immunoassay techniques are useful. The competitive and sandwich methods employ a phase separation step as an integral part of the method while steric inhibition assays are conducted in a single reaction mixture. Fundamentally, the same procedures are used for the assay of NF and for substances that bind NF, although certain methods will be favored depending upon the molecular weight of the substance being assayed. Therefore, the substance to be tested is referred to herein as an analyte, irrespective of its status otherwise as an antigen or antibody, and proteins which bind to the analyte are denominated binding partners, whether they be antibodies, cell surface receptors or antigens.

Analytical methods for NF or its antibodies all use one or more of the following reagents: labelled analyte analogue, immobilized analyte analogue, labelled binding partner, immobilized binding partner and steric conjugates. TThe labelled reagents also are known as "tracers".

The label used is any detectable functionality which does not interfere with the binding of analyte and its binding partner. Numerous labels are known for use in immunoassay, examples including enzymes such as horseradish peroxidase, radioisotopes such as $^{14}C$ and $^{131}I$, fluorophores such as rare earth chelates or fluorescein, stable free radicals and the like. Conventional methods are available to covalently bind these labels to proteins or polypeptides. Such bonding methods are suitable for use with NF or its antibodies, all of which are proteinaceous.

Immobilization of reagents is required for certain assay methods. Immobilization entails separating the binding partner from any analyte which remains free in solution. This conventionally is accomplished by either insolubilizing the binding partner or analyte analogue before the assay procedure, as by adsorption to a water insoluble matrix or surface (Bennich et al., U.S. Pat. No. 3,720,760), by covalent coupling (for example using glutaraldehyde crosslinking), or by insolubilizing the partner or analogue afterward, e.g., by immunoprecipitation.

Other assay methods, known as competitive or sandwich assays, are well established and widely used in the commercial diagnostics industry.

Competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers.

Another species of competitive assays, called a "homogeneous" assay, does not require a phase separation. Here, a conjugate of an enzyme with the analyte is prepared and used such that when anti-analyte binds to the analyte the presence of the anti-analyte modifies the enzyme activity. In this case, NF or its immunologically active fragments are conjugated with a bifunctional organic bridge to an enzyme such as peroxidase. Conjugates are selected for use with anti-NF so that binding of the anti-NF inhibits or potentiates the enzyme activity of the label. This method per se is widely practiced under the name of EMIT.

Steric conjugates are used in steric hindrances methods for homogeneous assay. These conjugates are synthesized by covalently linking a low molecular weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore.

Sandwich assays particularly are useful for the determination of NF or NF antibodies. In sequential sandwich assays an immobilized binding partner is used to adsorb test sample analyte, the test sample is removed as by washing, the bound analyte is used to adsorb labelled binding partner and bound material then separated from residual tracer. The amount of bound tracer is directly proportional to test sample analyte. In "simultaneous" sandwich assays test sample is not separated before adding the labelled binding partner. A sequential sandwich assay using an anti-NF monoclonal antibody as one antibody and a polyclonal anti-NF antibody as the other is useful in testing samples for NF activity.

The foregoing are merely exemplary diagnostic assays for NF and antibodies. Other methods now or hereafter developed for the determination of these analyte are included within the scope hereof, including the bioassay described above.

The following example is offered by way of illustration and not by way of limitation. All literature reference cited in the example section are expressly incorporated herein by reference.

EXAMPLE I

Preparation and Purification of Recombinant NF

Attempts to identify and isolate DNA encoding NF from a human genomic library using NGF and BDNF probes were unsuccessful. Instead, to identify the NF gene, it was necessary to amplify human genomic DNA using the polymerase chain reaction (PCR) (Mullis et al., *Cold Spring Harbor Symp. Quant. Biol.,* 51: 263 [1987]). Human genomic placental DNA (prepared as described in Maniatis et al. *Molecular Cloning: A Laboratory Manual,* Cold Spring Harbor Laboratory, New York (1982) in the section on preparing a genomic DNA library) was employed as template for the above-identified primers, since the active forms of both NGF and BDNF are encoded by a single exon (Leibrock et al., supra).

Amino acid sequences for NGF and BDNF were scanned for regions of common homology. A number of these regions were identified and single stranded primer pools containing restriction sites for Sal and Xba were prepared that were complementary to all possible sequences of DNA for the plus and minus strands of the selected NGF or BDNF sequences. The primer pool for the sense strand corresponded to residues 49–58 of (mature human βNGF) NGF. The sense primer comprised the following sequence of alternatives:

```
   protein seq.  .(F,L) K   Q   Y   F   F(Y) E   T   K   C
5' GTC GAC TCT AGA TC AAG CAG TAC TTC TAC GAG ACC AAG TG 3'
      Sal     Xba    G   A   A   T   T   TT  T   T   A
                                                       A
                                                       G
```

The primer pool for the antisense strand corresponded to residues 233–244 of BDNF and comprised the following sequence of alternatives:

```
                       C   V   C   A,S T   D   I   R   I   F   R   W
5' GTC GAC TCT AGA ACA TAC ACA GGA AGT GTC TAT CCG TAT GAA CCT CCA 3'
      Sal     Xba    G   C   G   A C C  A   G   T T G  A   T G
                                 A       T G         A       A
                                 G       C T
```

Thus, the sense and antisense primer pools contained, respectively, $2^8 \times 3^4$ (1536) and $2^9 \times 3^2 \times 4^3$ (294,912) individual sequences. Note that each primer sequence has a restricting site at its 5' end in order to facilitate cloning the amplified sequences. Careful selection of amplification conditions allowed us to amplify NF sequence despite the fact that these pools were considerably larger than the conventional pools used heretofore for shorter amino acid sequences (ranging from 32 to 32,000 fold degeneracy, see Lee et al., "Science" 239:1288–1291 [1988], Strathmann et al., "P.N.A.S. USA" 86:7407–7409 [1989], and Leibrock et al. supra). The primers were employed to prepare amplified DNA which was then sequenced. The conditions for amplification were as follows:

---

I. PCR with Human genomic placental DNA
   denat.     95° 5' once initially denat.    94° 1'
   anneal    55° 1'   } 33 cycles, repair with T4 polymerase
   extens.   72° 1'

10 μl 10× buffer (final = 50 mM KCl, 10 mM Tris pH 8.4, 3.0 mM MgCl$_2$
   3 μl human genomic DNA (3 μg)
   7.5 μl primer (approx. 1 μg = ~2.6 μM of 33 mer, therefore $10^3$ degen = nM, $10^6$ = pM)
   7.5 μl primer
   10 μl 10× dNTPs (final = 0.2 mM dNTPs)
   1 μl Taq polymerase
   61 μl dH$_2$O 100 μl V$_T$

---

Alternatively, the above amplification can be conducted using 45 cycles (95° C., 55° C., 72° C. for 1 minute each) followed by 15 minutes at 72° C. with 7.5 ng/μl of each primer to obtain the same results.
II. Cut with Xba, generate and gel purify fragments of the expected size, about 210 bp, and subclone into pUC-based vector (Yanish-Perron et al., *Gene*, 33:103 (1985)) or Bluescript plasmid (Stratagene).

NGF or BDNF clones were identified by hybridization with oligonucleotides derived from unique regions of their respective cDNA sequences. Plasmids containing non-hybridizing inserts were sequenced (Smith, *Meth. Enzymol.*, 65: 560 (1980)) and their potential translation products were analyzed for homology with NGF and BDNF.

This procedure revealed the presence of 30 NGF, 27 BDNF, and 5 unrelated clones. In addition, a single DNA fragment encoding part of a novel NGF-related factor was identified and designated NF or NT-3. The low abundance of NF clones generated by PCR was caused by the poor homology between its DNA sequence and the PCR primers. The sequence of the NF DNA was determined and found later to have some errors, due in part to the relatively high error frequency of Taq polymerase.

In order to obtain NF cDNA (to confirm sequence and secure the regions not present in the sequenced clone), a human fetal brain cDNA library (Rosenthal et al., *EMBO J.*, 6: 3641 (1987)) and a rat adult forebrain cDNA library (L. Coussens et al., *Science*, 233: 859 (1986)) were screened using the genomic placental clone as a probe. The human cDNA library yielded two 600-bp partial human cDNAs that were subsequently isolated by conventional techniques. The rat library yielded clone 39, a 1.2–1.3 Kb cDNA clone containing an open reading frame spanning 258 amino acids (encoding the full-length sequence of rat NF). This confirms that the NF sequence is not a pseudogene, with expression occurring normally in human and animal cerebral cortex during development and in the adult. To obtain a complete human NF homolog, a human genomic library was also screened (Maniatis et al., *Cell,* 15: 687 (1978)) and a 1.9 kb DNA fragment was isolated. This fragment was found to contain a single open reading frame encoding a polypeptide of 257 amino acids starting 21 bp downstream of an intron acceptor site, on a single exon, encompassing the NF precursor polypeptide.

The full nucleotide sequence and deduced amino acid sequence of human precursor NF is shown in FIG. 1. Assignment of the initiation codon was based on homology with the rat NF, and its amino acid sequence is 44.2% and 38.5% homologous to NGF and BDNF precursors, respectively. The sequence of the mature portion was derived from the two cDNA clones, and the sequence of the region 5' to the N-terminus of the mature region was derived from the genomic clone.

The active mature forms of both NGF and BDNF are homodimers of 13–14 kD proteins that are generated from their ca. 30 kD precursors (Leibrock et al., supra, and Greene and Shooter, *Ann Rev. Neurosci.*, 3: 353 (1980)). The NF precursor protein sequence also showed a potential tetrabasic cleavage site at Arg$^{138}$, indicating that all three members of this protein family may be similarly processed. Processing at this site would result in a 13.6 kD (119 amino acid) polypeptide having 57.6% and 55.6% identity to NGF and BDNF, respectively. The rat and human precursor proteins (preproNF) differ by only 12 amino acids. The putative mature form of the two substances is identical in amino acid sequence.

The full nucleotide sequence and deduced amino acid sequence of rat precursor NF is shown in FIG. 2 and is derived from clone 39. The start of the mature region is indicated by an arrow.

To assess the possible function of NF, its tissue distribution was determined by Northern blot analysis. In the rat, NF mRNA was found in varying levels in heart, kidney, liver, spleen, and lung, and in several brain regions, including cerebellum, medulla oblongata, and hippocampus. This broad organ localization of NF mRNA suggested that in the peripheral nervous system, NF could serve as a target-derived trophic factor for sympathetic and/or sensory neurons. This theory was tested by expressing DNA encoding recombinant human NF and testing its various activities.

A cytomegalovirus-based expression vector called pRK5, described in Gorman et al., *DNA and Protein Engineering Techniques,* 2: 1 (1990) and in EP publication number 307,247 published Mar. 15, 1989, was employed as the expression vector. The NF genomic DNA was cut from the phage in which it was cloned using BglII and HindIII. This DNA fragment, which contained the single exon encoding the preproNF, was then ligated into pRK5 previously cut with BamHI and HindIII using standard ligation methodology (Maniatics et al., *Molecular Cloning: A Laboratory Manual,* Cold Spring Harbor Laboratory, New York (1982)). The resulting vector was called pRK-5hNT-3.

A human embryonal kidney 293 cell line (Graham et al., *J. Gen. Virol.,* 36: 59 (1977)) was grown to confluence. Ten $\mu$g of the NF plasmid DNA (pRK-5hNT-3) was mixed with 1 $\mu$g of DNA encoding the VA RNA gene (Thimimappaya et al., *Cell,* 31: 543 (1982)) and dissolved in 500 $\mu$l of 1 mM Tris-HCl, 0.1 mM EDTA, 0.227 M $CaCl_2$. Added to this (dropwise while vortexing) was 500 $\mu$l of 50 mM HEPES (pH 7.35), 280 mM NaCl, 1.5 mM $NaPO_4$, and the precipitate was allowed to form for 10 min. at 25° C. The suspended precipitate was then added to the cells (in 100 mM plate) and allowed to settle for four hours in the incubator. The medium was then aspirated off and 2 ml of 20% glycerol in phosphate-buffered saline was added for 30 sec. The cells were washed twice with 5 ml of serum-free medium, then fresh medium was added and the cells were incubated for five days.

The 293 cells were also transfected in the same way with pRK5 alone.

Twenty-four hours after the transfection, the medium was replaced and cells were incubated for 12 hours in the presence of 200 $\mu$Ci/ml $^{35}$S-cysteine and 200 $\mu$Ci $^{35}$S-methionine. Conditioned medium was then collected, concentrated 5-fold by lyophilization, and loaded on a 15% SDS gel, which was subsequently enhanced, dried, and exposed to film for two hours. This data indicated the presence of two secreted NF isoforms, a 17–18 kD protein, possibly a processed NF corresponding to a dibasic cleavage site at $Arg^{98}$, and a polypeptide of approximately the expected size (14–15 kD).

Large-scale expression of NF was performed by transiently introducing by the dextran sulfate method (Sompayrac and Danna, *Proc. Natl. Acad. Sci. USA,* 12: 7575 (1981)) 700 $\mu$g of pRK-5hNT-3 into the human embryonal kidney 293 cell line grown to maximal density (1.5 liters) in a 3-liter Belco microcarrier spinner flask. The cells were first concentrated from the spinner flask by centrifugation, and washed with phosphate-buffered saline (PBS), and the DNA-dextran precipitate was incubated on the cell pellet for four hours. The cells were treated with 20% glycerol for 90 seconds, washed with a medium such as 50:50 DMEM:F-12 medium, and re-introduced into a 3-liter spinner flask containing 1.5 liter of the above medium plus 5 $\mu$g/ml bovine insulin and 0.1 $\mu$g/ml bovine transferrin. The above protocol was performed for three separate 3-liter cultures.

After 4 days approximately 5 liters of conditioned media from the large-scale expression described above was centrifuged and filtered to remove cells and debris, and concentrated 100-fold. The buffer, salts, and other small molecules were exchanged by dialysis into 25 mM sodium borate, ph 9.0, and 4 M urea, and applied to a 5 cm.×5 cm. DEAE Sepharose Fast-Flow ion-exchange chromatography column (Pharmacia, Inc.). The pH of column effluent (495 ml) was neutralized (pH 7.0) by the addition of 0.1 volume of 250 mM 3-(N-morpholino)propanesulfonic acid (MOPS) buffer to give a final composition of 25 mM MOPS, pH 7.0, and 4 M urea. This sample was applied to a 2.5 cm.×2.5 cm. S-Sepharose ion-exchange chromatography column (Pharmacia, Inc.), washed, and eluted with 25 mM MOPS, pH 7.0, 4 M urea, and 0.5 M NaCl (40 ml).

Two different assays indicated the presence of recombinant human NF in the S-Sepharose salt eluant (130 ng/ml, 5 $\mu$g total): 1) 48-hour neuronal survival and neurite outgrowth in three types of chick embryonal peripheral ganglionic neurons: paravertebral sympathetic chain ganglion neurons, spinal sensory neurons of dorsal root ganglia (lumbosacral region), and nodose ganglion neurons, and 2) immunocrossreactivity in an ELISA assay (Lucas et al., *J. Endocrinol.,* 120: 449–457 (1989)) utilizing polyclonal antibodies to human $\beta$-NGF, which can be generated as described above in the Description Section using $\beta$-NGF as immunogen rather than NF. The S-Sepharose eluant was dialyzed into 1 M acetic acid and 4 M urea, concentrated 10-fold, applied to a S-300 Sephacryl gel-filtration column (1.5 cm.×44 cm.), and chromatographed in the same buffer. Immunocrossreactivity and neuronal survival bioassays indicated an early-eluting, broad peak of activity and a later-eluting, single peak of activity.

Aliquots of 200 $\mu$l were taken from each 1 ml fraction collected, dialyzed against 1 M acetic acid, lyophilized, and redissolved in 30 $\mu$l Laemmli SDS-PAGE sample buffer (Laemmli, *Nature,* 227: 680–685 (1970)). Human $\beta$-NGF was obtained in a similar manner. Following SDS-PAGE, the silver-stained gel indicated a single, prominently stained polypeptide of approximately 15 kD. A 3-ml pool of S-300 column eluted fractions corresponding to this SDS-PAGE analyzed region was made, and 1 ml (0.5 nmole) was submitted to N-terminal amino acid sequence analysis by Edman degradation performed on a prototype automated amino acid sequencer (Kohr, EP Pat. Pub. No. 257,735). N-terminal sequence analysis of 52 amino acid residues gave a single sequence starting with a tyrosine residue predicted by the tetrabasic cleavage sequence starting with a tyrosine residue predicted by the tetrabasic cleavage sequence ending at $Arg^{138}$ and predicted by the processing of preproNGF to mature $\beta$-NGF.

The quantitation of the initial sequencing cycles (370 pmole tyrosine, 75% initial recovery in first sequencing cycle) indicated a recovery of 20 $\mu$g of purified recombinant human NF from the three-column process. The purified recombinant human NF was dialyzed into 0.1% acetic acid to give a final concentration of 3.25 μg/ml. This stock material was diluted into neuronal cell media (DMEM high glucose with 10% fetal bovine serum) at various concentrations from 4 to 60 ng/ml.

EXAMPLE 1

Assays of NF

Purified NF was analyzed for neurotrophic activities on several types of primary embryonal day-10 chick neurons as described by Davies, in Nerve Growth Factors, R. A. Rush, ed. (John Wiley & Sons, Ltd., Boston, Mass., 1989), pp. 95–109. Thus, paravertebral sympathetic chain ganglia (SG), dorsal root (lumbosacral) ganglia (DRG), and nodose ganglia (NG) were dissected from day-10 chick embryos. The neuronal cells were dispersed from the ganglia with trypsin or pancreatin (GIBCO) and preplated twice to reduce the number of non-neuronal cells. Cells were counted and seeded in a 96-well tissue culture plate that had been pretreated with polyornithione (500 μg/ml) and laminin (10 μg/ml). (Lindsay et al., Dev. Biol., 112: 319 (1985)). The cell seeding numbers were SG and DRG, 4000 cells per well; NG, 2000 cells per well.

Purified mouse submaxillary gland β-NGF used in the assays was obtained from Biomedical Technologies, Inc. and dissolved in 0.1% acetic acid to a concentration of 10 μg/ml. Purified recombinant human NF from Example I was dialyzed into 0.1% acetic acid to give a final concentration of 3.25 μg/ml. Cells were incubated with or without factors for 48 hours and phase-bright cells bodies which has elaborated neurites 5x the length of the cell body were counted. Individual perikaryons could be counted in the cultures of DRG and NG neurons. However, the perikaryons of SG neurons aggregate and cell aggregates were scored. The cell survival at maximal response was approximately 20–40% for DRG and NG neurons, whereas SG neurons are likely higher since aggregates were scored. The experimental result was representative of four experiments utilizing pure factor. The relative $EC_{50}$ (effective concentration for half-maximal response) for NGF- and NF-dependent sympathetic neuronal survival was approximately 0.4 and 6 ng/ml, respectively.

NF was the most potent in promoting neurite outgrowth from embryonic day-10 sympathetic neurons (FIG. 4A). In the absence of NF, very little neurite outgrowth and extensive degeneration of nerve cell bodies were observed. Following the addition of NF for 48 hours, approximately 30% of the cells formed extensive neuritic networks and perikaryons appeared large and phase-bright. The effect was dose dependent over a wide range of concentrations, and although the maximal response was indistinguishable from the one obtained by NGF, NF was typically 10–20-fold less active on a molar basis (FIG. 4A).

Surprisingly, NGF and NF differ in their activity on peripheral sensory neurons. In vertebrates, peripheral sensory neurons are derived from two distinct embryonic sources: the neural crest and the neural placodes (LeDouarin and Smith, Ann. Rev. Cell Biol., 4: 375 (1988)). Neural crest-derived cells give rise to neurons and to the supporting cells of the peripheral nervous system and the placode-derived cells give rise to some sensory cells and cranial neurons.

The neural crest-derived dorsal root sensory ganglia (DRG) cells project to the CNS and to peripheral tissues, and are dependent on neurotrophic factors derived from both targets. Lindsay et al., Dev. Biol., 112: 319 (1985). This dual dependency is a possible mechanism to ensure the survival only of neurons that form all the appropriate connections. Placode-derived nodose sensory ganglia (NG), which are also dually connected and respond to the CNS factor BDNF, do not respond to the peripherally derived trophic factor (NGF). Thus, peripheral target innervation by NG neurons is likely to be ensured by an alternative mechanism or via other factors.

Figure 4B:
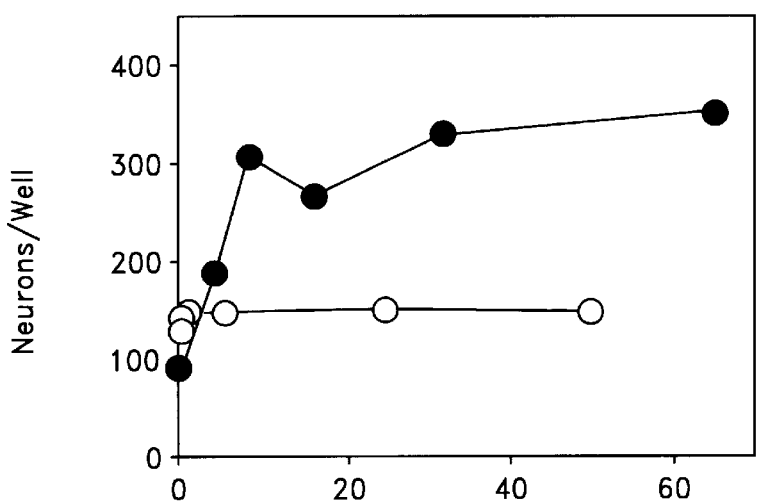
Figure 4C:
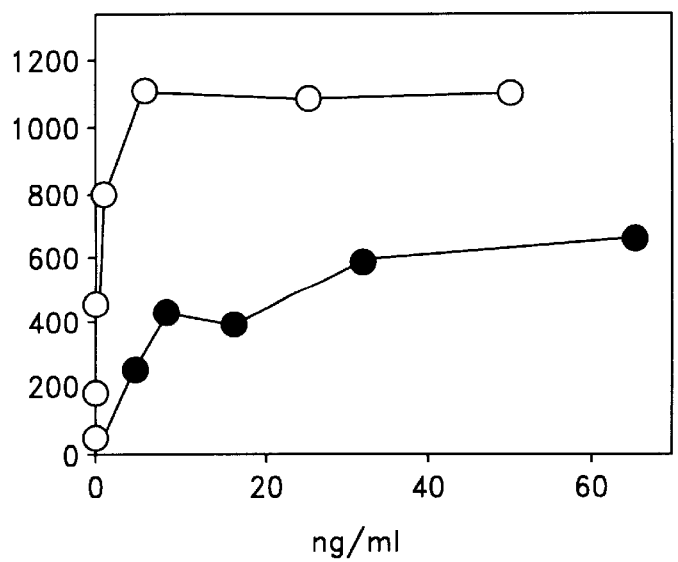

In this assay, NF was found to have neurotrophic activity on embryonic day-10 chick NG neurons (FIG. 4B), suggesting that it can function as a trophic agent for placode-derived peripheral sensory neurons. NF also displayed neurotrophic activity on DRG neurons, but its effect on these cells were smaller than that observed with NGF (FIG. 4C). Thus, neural crest-derived DRG sensory neurons respond primarily to NGF, while placode-derived NG sensory neurons respond primarily to NF. The activity of individual trophic factors is not always limited to neurons derived from one embryonic tissue. (Lindsay et al. supra). Rather, without being limited to any one theory, neurons originating from the same embryonal source may respond to distinct trophic factors because they have different target specifities (Davies, Development Supplement, 103: 175–183 (1988)). Thus, NG sensory neurons that innervate visceral tissues, and DRG sensory neurons that innervate mainly somatic tissues may respond to distinct trophic factors because they have different target specifities. The fact that DRG neurons are supported by NF to some extent may be due to the fact that these ganglia contain a mixed population of neurons, some of which project to visceral tissues.

NG cells are less sensitive to NF as compared to sympathetic neurons. Without being limited to any one theory, this may again reflect the fact that the nodose ganglia contain a mixed population of neurons that project to different peripheral targets. NG neurons innervate both special and general visceral tissues, and these two classes of neurons could be differentially responsive to NF. An alternative explanation is that the dependence on NF is developmentally restricted and that embryonic day-10 sensory neurons are less responsive to this factor as compared to neurons from earlier or later embryonic stages. Another explanation is that NG cells may be intrinsically less responsive to NF than sympathetic neurons. It was found that NF, like NGF, does not display any neurotrophic activity on parasympathetic ciliary ganglion cells.

In addition to its activity as a trophic factor, NF was found to be a potent differentiation inducing agent for rat phaeochromocytoma cell line (PC-12), obtained from Dr. L. Reichardt (University of California at San Francisco) and grown as described by Greene and Tischler, Proc. Natl. Acad. Sci. USA, 73: 2424 (1976). Cells were seeded (5000/well) into 24-well Primaria cationic plates (Falcon) and allowed to attach overnight. Cell media was removed and replaced with DMEM high glucose supplemented with N2 medium (Bottenstein and Sato, Proc. Natl. Acad. Sci. USA, 76: 514 (1978)) either alone, with mouse β-NGF (50 ng/ml), or with human recombinant NF (60 ng/ml). After three days, the percentage of neurite elaborating cells was determined microscopically. The average percentages of neurite-bearing cells at these doses were 75% for NGF and 71% for NF. Thus, as with NGF, addition of NF to these cells promoted neurite outgrowth and induced neuronal phenotype in these cells.

The actual physiological role of NF as a neurotrophic and differentiation inducing factor in vivo is not known. Prior to the identification of NF, NGF was thought to be the only embryonal trophic factor for sympathetic neurons. This conclusion arose since anti-NGF antibodies mediated the destruction of these neurons in vivo (Levi-Montalcini, in *Immunosympathectomy*, Steiner and Schoenbaum, eds. (Elsevier, Amsterdam, 1972), pp. 55–78), and since exogenously administered factor reduced the extent of their naturally occurring death. This exclusive role of NGF should be re-evaluated, since, for example, it is possible that cross-reactivity of the NGF antibody with NF could account for the destruction of sympathetic cells in vivo.

Alternatively, although a saturated dose of a single factor is sufficient for neuronal survival in culture, the physiological level of each factor might be inadequate. In vivo, therefore, both factors could be required to support the survival of sympathetic cells.

The need for a second trophic factor for peripheral sensory neurons is predicted from the data presented herein showing that NGF support only a subset of these cells. While the need for an additional, apparently redundant, trophic factor for sympathetic neurons is not as evident, such a factor could participate in defining precise innervation sites or replace NGF during certain embryonic stages.

The presence of NF in the CNS and the periphery suggests additional functions and raises the possibility that it could be valuable for treating diseases such as Alzheimer's, Parkinson's, or Huntington's chorea that are caused by brain neuron degeneration and/or treating damaged nerves due to trauma. NF could be tested for such functions in an established animal lesion model such as that of Hefti, supra, or in aged rats or monkeys.

In summary, NF displays a novel trophic activity on sympathetic and placode-derived peripheral sensory neurons with a broad tissue distribution. It complements NGF and BDNF, which are trophic factors for some, but not all, peripheral neurons. Each of these factors can likely act alone or in concert on defined subsets of neurons to achieve the correct neuronal connections both in the peripheral and central nervous system.

What is claimed is:

1. An isolated nucleic acid, comprising the nucleotide sequence shown in FIG. 2 that encodes rat precursor NT-3.

2. The isolated nucleic acid of claim 1, consisting of the nucleotide sequence shown in FIG. 2 that encodes rat precursor in NT-3.

3. The isolated nucleic acid of claim 1, comprising the cDNA sequence shown in FIG. 2.

4. A vector comprising the nucleic acid of claim 1.

5. The vector of claim 4, comprising a bacterial promoter operably linked to the nucleic acid sequence shown in FIG. 2 that encodes rat precursor NT-3.

6. The vector of claim 5, wherein the promotor is inducible.

7. The vector of claim 6, wherein the promoter is an alkaline phosphatase promoter.

8. The vector of claim 4, further comprising a nucleic acid encoding a secretion signal peptide operably linked to the nucleic acid sequence shown in FIG. 2 that encodes rat precursor NT-3.

9. The vector of claim 8, wherein the signal peptide is an *E. coli* STII peptide.

10. A recombinant host cell, comprising the nucleic acid of claim 1.

11. The recombinant host cell of claim 10, wherein the host cell is mammalian.

12. The recombinant host cell of claim 11, wherein the mammalian host cell is selected from the group of cell lines consisting of VERO, HeLa, Chinese hamster ovary, WI38, Baby hamster kidney, COS-7, MDCK, and human embryonic kidney cell line 293 cells.

13. The recombinant host cell of claim 10, wherein the host cell is prokaryotic.

14. The recombinant host cell of claim 13, wherein the host cell is *E. coli*.

15. A method for producing rat precursor NT-3, comprising culturing the host cell of claim 10 under conditions suitable to express rat precursor NT-3 and recovering rat precursor NT-3 from the host cell culture.

16. The method of claim 15, wherein the nucleic acid further comprises a nucleic acid sequence encoding a secretion signal peptide operably linked to the nucleic acid sequence shown in FIG. 2 that encodes rat precursor NT-3.

* * * * *